United States Patent [19]

Simon

[11] Patent Number: 4,857,274

[45] Date of Patent: Aug. 15, 1989

[54] DEVICE FOR ANALYZING A LIQUID SAMPLE

[75] Inventor: Jean-Pierre Simon, Grenoble, France

[73] Assignee: Kis Photo Industrie, France

[21] Appl. No.: 64,696

[22] Filed: Jun. 22, 1987

[30] Foreign Application Priority Data

Jun. 26, 1986 [FR] France ................. 86 09488

[51] Int. Cl.$^4$ .............................. G01N 9/30
[52] U.S. Cl. ..................... 422/72; 356/426; 356/427; 422/102; 128/770; 128/771
[58] Field of Search .......................... 422/61, 72, 102; 436/165, 177, 180; 356/426, 427; 250/576

[56] References Cited

U.S. PATENT DOCUMENTS

| 3,713,775 | 1/1973 | Schmitz | 422/72 |
|---|---|---|---|
| 4,462,964 | 7/1984 | Guigan | 422/72 |
| 4,690,899 | 9/1987 | Klose et al. | 422/72 |
| 4,714,590 | 12/1987 | Guigan | 422/72 |

FOREIGN PATENT DOCUMENTS

| 0073512 | 3/1983 | European Pat. Off. | 422/72 |
|---|---|---|---|
| 0160282 | 11/1985 | European Pat. Off. | |
| 0180528 | 5/1986 | European Pat. Off. | |
| 2524674 | 10/1983 | France | 422/72 |

OTHER PUBLICATIONS

Schultz, Steven G., "Two-Dimensional Centrifugation for Desk-Top Clinical Chemistry", Clinical Chemistry, vol. 31, No. 9, 1985, pp. 1457-1463.

*Primary Examiner*—Michael S. Marcus
*Attorney, Agent, or Firm*—Arnold, White & Durkee

[57] ABSTRACT

A device for analyzing a liquid sample such as blood includes a cartridge portion and a casing portion. The cartridge includes an inlet for directly receiving a sample. The cartridge is then irreversibly clipped to the casing so that an inlet of the casing is in communication with an outlet of the cartridge. The sample is then mixed in the casing with a diluent and/or reagent by using a centrifuge, and measurements are taken. The device allows a sample to be taken directly into the cartridge, and restricts employment of the device to a single use.

7 Claims, 9 Drawing Sheets

DEVICE FOR ANALYZING A LIQUID SAMPLE

BACKGROUND OF THE INVENTION

The present invention relates to the analysis of a liquid sample. The invention will be described and explained hereinafter by reference to the biomedical monoparametric analysis of a sample of whole blood, but it must be understood that the present invention cannot be limited in its scope to this field of activity.

In accordance with Patent Application EP-A-No. 0,180,528, a device for analyzing a liquid sample has been described, comprising a compartmented casing, having the shape of a disk and possessing:

a container for at least one dose of a reagent and/or a diluent;

a chamber for calibration of a calibrated quantity obtained from the sample;

a chamber for mixing at least the calibrated quantity and the dose of reagent;

and, if required, an optical measurement cell communicating with the mixing chamber.

And the casing is intended to interact with a centrifuging apparatus, for the purpose of causing the liquids to circulate within the said casing under the action of the force of the centrifuge.

According to this patent application, in addition to the analytical device as such, there is also provided, fixed to the casing, an introduction device with stopper, which is intended to receive a portion (for example a few drops) of the sample to be analyzed.

If the solution according to Patent Application EP-A-No. 0,180,528 is used to analyze, for example, a plasma sample, this entails manipulating the said sample in addition to the necessary prior centrifuging of the sample of whole blood. This may result, first, in the loss of all or some of the sample to be analyzed, and secondly in contamination of the said sample, falsifying or preventing the subsequent analysis.

Moreover, with the above introduction device, there is never any certainty that the quantity introduced is sufficient for analysis. Alternatively, it is necessary to work with a greatly excessive quantity of sample, and there is then the risk of saturating the analytical device, with no further possibility of obtaining a reliable measurement.

The present invention relates to an analytical device permitting direct sampling of a determined and reliable quantity of the liquid to be analyzed.

According to the invention, the device comprises an independent cartridge which can be irreversibly clipped onto the casing and which comprises an inlet for introducing the sample to be analyzed, a receptacle for collecting the sample introduced, a means for metering the collected sample, connected to the receptacle via a capillary duct, and an outlet for a metered quantity towards a casing inlet which communicates with the calibration chamber of the said casing.

By virtue of the invention it is possible to take the sample to be analyzed directly with the cartridge, the sample always being limited to the same initial quantity, by virtue of the receptacle which is stoppered at the side opposite the inlet by the capillary duct. Subsequently, the cartridge being permanently clipped to the casing, it is possible to meter the sample into the cartridge, in order to introduce an exact and reliable quantity into the interior of the analysis casing as such.

Liquid, for the purposes of the present invention, is understood to mean any fluid capable of flowing, whether it be a liquid, a suspension or any other substance whose viscosity is compatible with flowing within the analytical device.

The manner in which the invention can be implemented, and the advantage deriving therefrom, will be more clearly apparent from the example of embodiment which follows, given by way of non-limiting indication, with reference to the attached figures.

DESCRIPTION OF THE REFERRED EMBODIMENTS

Figure 1:
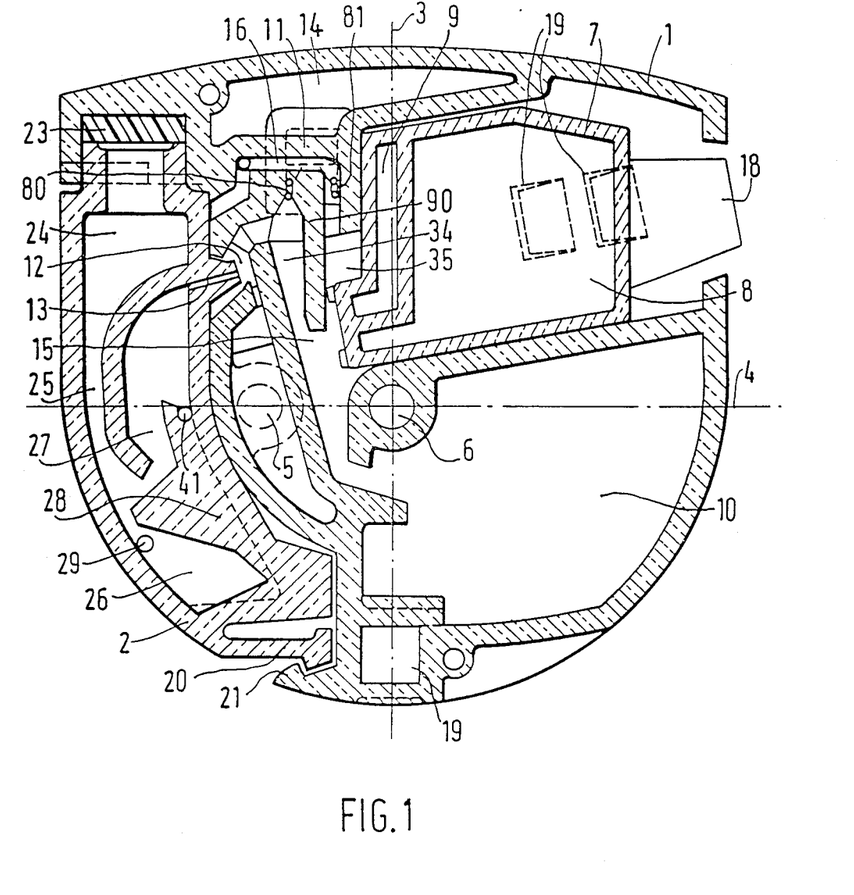
FIG. 1 is a section along a horizontal plane of an analytical device according to the invention.

As may be seen in FIG. 1, the device according to the invention comprises two distinct parts, a casing (1) and an independent cartridge (2), the latter being intended to be clipped onto the casing in an irreversible manner at the time of use. The analytical device thus formed is flat, and when in use possesses a generally shield-shaped appearance; it is placed in accordance with a substantially horizontal principal plane, on the disk of a centrifuge. The irreversibility of the clipping of the cartridge to the said casing restricts the employment of the device to a single use.

The casing (1) possesses, along one of the two median axes (3, 4), two apertures (5, 6) intended to interact with positioning pins located on the disk of the centrifuge and positioned respectively one at the point of intersection (6) of the two median axes (3, 4) and the other (5) offset along the axis (4). The axis (3) corresponds to the centrifuging axis, as explained hereinafter, in one direction or the other, in other words downward or upward according to FIG. 1. The interaction of the positioning pins with the apertures (5, 6) makes it possible to alternate the centrifuging direction, as explained in the French patent application filed in the name of the present Applicant Company on 25th September 1986 under No. 86/13,550.

The casing (1) is compartmented into a plurality of chambers, the majority of which are mutually interconnected by means of capillary ducts or apertures. Capillary duct or aperature, for the purposes of the present invention, is understood to mean any means permitting, first, in the absence of any centrifugal force, a liquid to be halted on meeting any natural flow, for example due to gravity, and secondly, in the presence of a centrifugal force, capable of acting as a flow aperture or duct for the same liquid.

The partitions defining the various chambers are produced directly by molding. Like the base and the lid, the said partitions are made from methyl polymethacrylate, a material which, as is known, is particularly transparent to ultraviolet radiation, which permits various optical analyses involving the use of wavelengths in the vicinity of 340 nm, that is to say in the ultraviolet range.

In a conventional manner, the base and the lid of the casing (1) are fixed to the partitions by ultrasonic welding.

Figure 5:
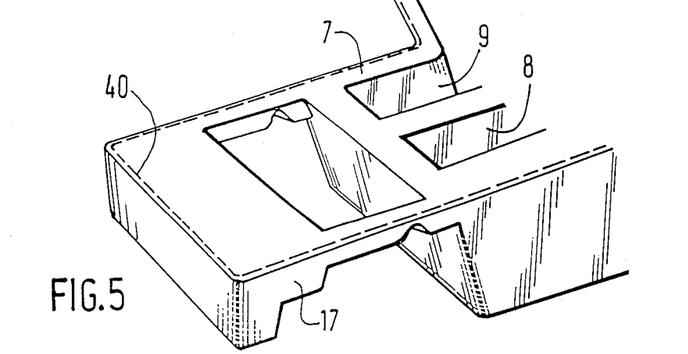
FIGS. 5 to 10 are diagrammatic representations of the covering device for the reservoir assembly and of its mode of operation in accordance with the invention.

The various compartments define, respectively:

in the upper right quarter, defined by the two median axes (3, 4), a compartment for the reservoir assembly (7) formed by the joining of the container for the diluent (8) [for the reagent] and the container for the reagent (9) (cf. FIG. 5);

in the lower right quarter, defined by the two median axes (3, 4), a mixing chamber (10) first for the doses of diluent and reagent contained respectively in the containers (8) and (9), and secondly for the combination of diluent/reagent with a calibrated quantity of the liquid to be analyzed;

in the upper left quarter, defined by the two median axes (3, 4), a calibration chamber (11) for the liquid to be analyzed, communicating:

first with an inlet (12) in the shape of a frustoconical funnel, provided on one of the edges of the casing (1), communicating with the capillary outlet (13) of the separation cartidge (2) when the latter is permanently clipped onto the casing;

secondly, via a duct (16), with an overflow chamber (14) for the liquid to be analyzed, situated in the lower part of the casing (1);

and finally, with the mixing chamber (10), via a capillary transfer duct (15).

The calibration chamber (11) is in the shape of a metering siphon whose principal axis is parallel to the axis (3). It is positioned below the plane of circulation of the liquids (diluent, reagent, metered quantity originating from the cartridge (2)), in the first part of the casing, towards the mixing chamber (10), broadly the lefthand half according to FIG. 1; which means that in this first part the casing possesses two levels separated by a planar median partition (not shown).

The calibration chamber (11) communicates with the inlet (12) via a capillary introduction duct (80), and via a capillary drainage duct (81) with the transfer passage (15). The drainage duct (81) also communicates via the duct (16) with an overflow chamber situated on the lower level of the casing. Ducts (80) and (81) are separated, for the purpose of the circulation of the liquids, by a partition (90).

Figure 1A:
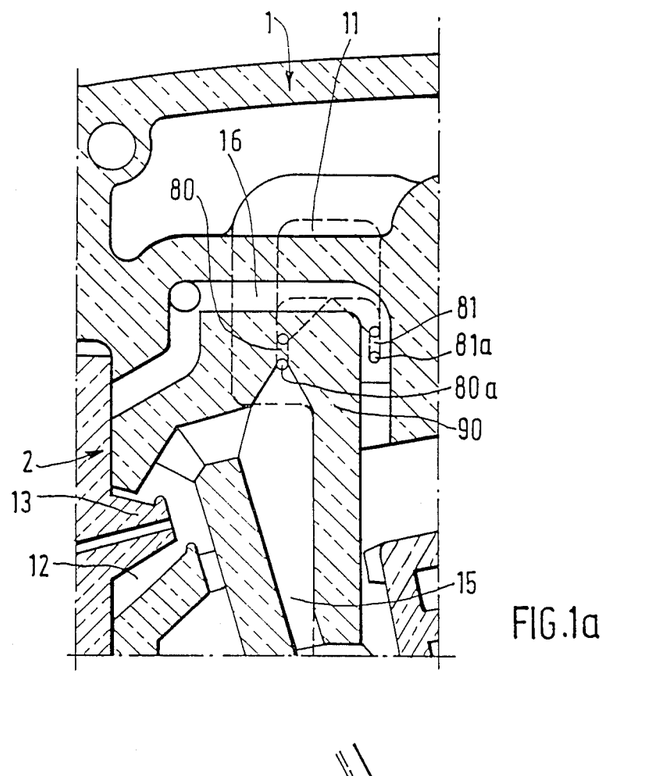
FIG. 1a represents a view on an enlarged scale of the casing shown in FIG. 1, at the level of the calibration chamber.
Figure 2:
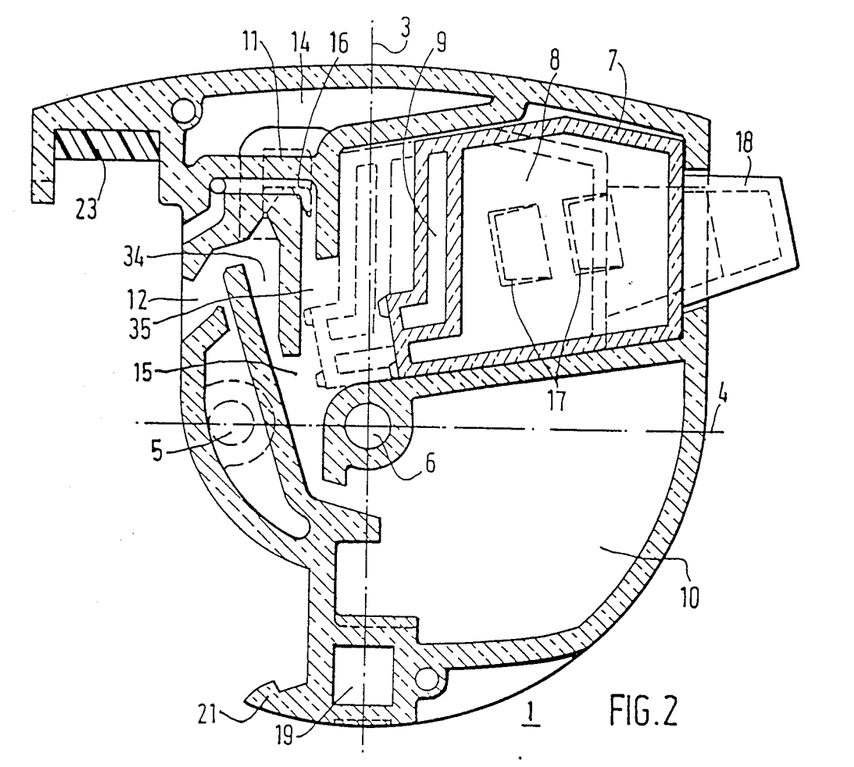
FIG. 2 is a section along the same plane of the casing belonging to the device according to FIG. 1, showing the two positions of the container for the reagent and the diluent, one in solid lines and the other in broken lines.

The inlet aperture (80a) of the capillary introduction duct and the outlet aperture (81a) of the capillary outlet duct (cf. FIG. 1a) are situated at the level of the abovementioned median partition, that is to say above the calibration chamber (11). The ducts for introduction (80) and drainage (81) are inclined, relative to the principal plane of the casing (1), towards the calibration chamber (11) situated below.

With the calibration chamber according to the invention, the upward action of the centrifugal force along the axis (3), combined with the positioning of the said chamber, makes it possible to level off the excess liquid at the level of the aperture (81a) and to obtain a precise and exact calibration.

The receptacles for the diluent (8) and the reagent (9) are placed in an independent compartment (7) which acts in the manner of a drawer. In fact, in order first to facilitate filling operations and secondly to permit the reagent to be stored for substantial periods, the reservoir assembly (7) is produced independently of the casing (1) by molding in polyolefin. It is then filled with one or more reagents, and their respective diluents. Finally, it is sealed by means of a cover (40) formed by a complex aluminoplastic film, in order to ensure total insulation of the reagent or reagents from the external atmosphere. As can be better seen in FIGS. 6 to 10, the reservoir assembly (7) has in the vicinity of one of its ends a lug (17), referred to as a retaining lug.

Figure 6:
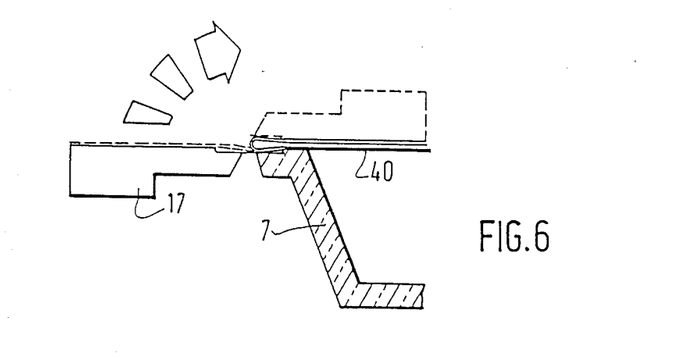

At the time of sealing, the cover (40) is likewise applied to this lug (17). In FIG. 6 the profile of the said cover has been shown in broken lines, once it has been folded back on the assembly (7). As can be seen in FIG. 5, the reservoir assembly (7) is positioned in the casing (1) (whose top lid has not yet been welded on), and the retaining lug (17) is folded back upwards, the effect of which is to break the two plastic connecting arms.

Figure 7:
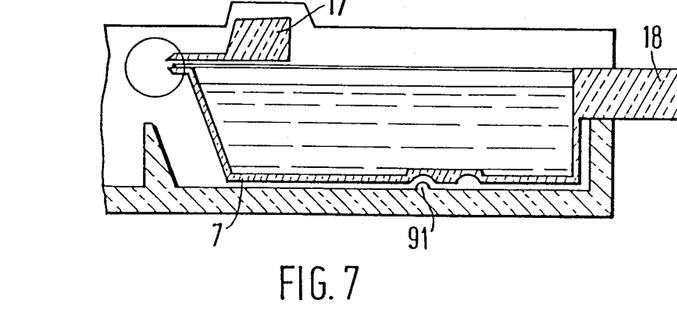
Figure 8:
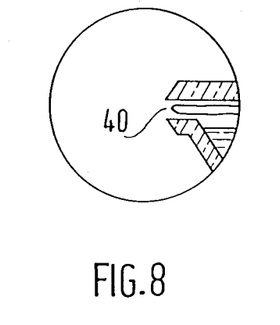
Figure 9:
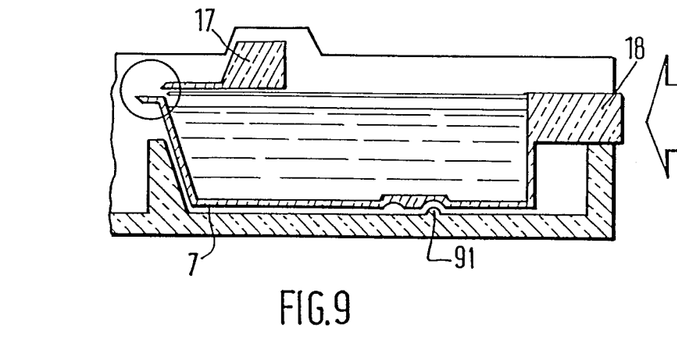
Figure 10:
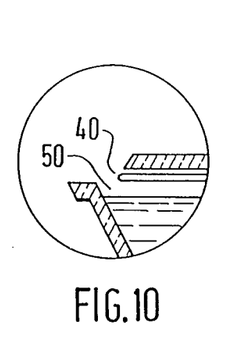
Figure 11:
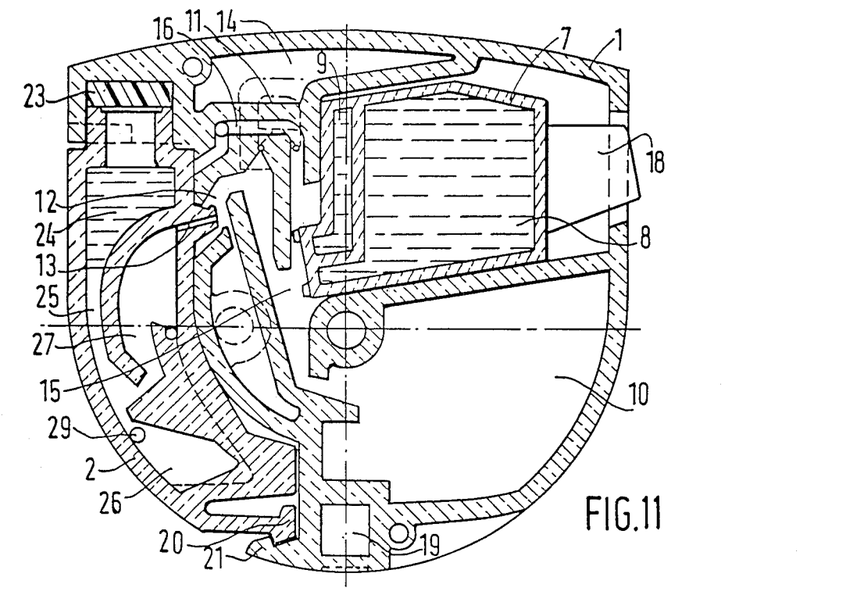
FIGS. 11 to 16 represent diagrammatically the operation of a device according to the invention.

The lid is then ultrasonically welded onto the housing (1), the retaining lug coming to rest in a hollow provided for this purpose in the said lid. In addition, the reservoir assembly (7) possesses a push-button (18) which projects from the casing (1) on the side opposite to the retaining lug (17). Finally, the reservoir assembly (7) possesses in its lower part a clipping system (19) intended to interact with the base of the casing (1). When the push-button (18) is actuated, the reservoir assembly (7) is irreversibly moved from the reagent and diluent conservation position shown in FIG. 8, in which the assembly (7) is sealed in a leak-tight manner, into a definitive operating position. As can be better seen in FIGS. 7 to 10, and from the fact of the immobility of the retaining lug (17), the movement of the said assembly (7) causes the detachment of the cover (40) over a length which is half the length of the movement of the reservoir assembly (7). As the two containers (8, 9) are contiguous at the level of this end, the liquids which they contain can be released through the capillary aperture (50) thus created, during the centrifuging phases, towards the mixing chamber (10). FIGS. 7 and 10 show, diagrammatically, enlarged views of this aperture (50), before and after the irreversible clipping of the reservoir assembly (7) onto the casing (1).

However, it must be noted, and it is an important feature of the invention, that without the action of a centrifugal force the liquids cannot be freely drained out of the assembly (7), because the aperture (50) caused by the detachment is not only positioned on the upper part of the reservoir assembly (7) but also of a capillary nature.

The measuring cell (19) communicates freely with the mixing chamber (10). In a conventional manner, it possesses two walls with parallel faces, having a good optical quality, in order to allow spectrophotometric measurements.

The separation cartridge (2) possesses (cf. FIG. 3) a generally arcuate appearance. It is intended to fit inside and be irreversibly clipped to the casing (1), by means of interacting clipping members (20, 21).

Figures 3, 4:
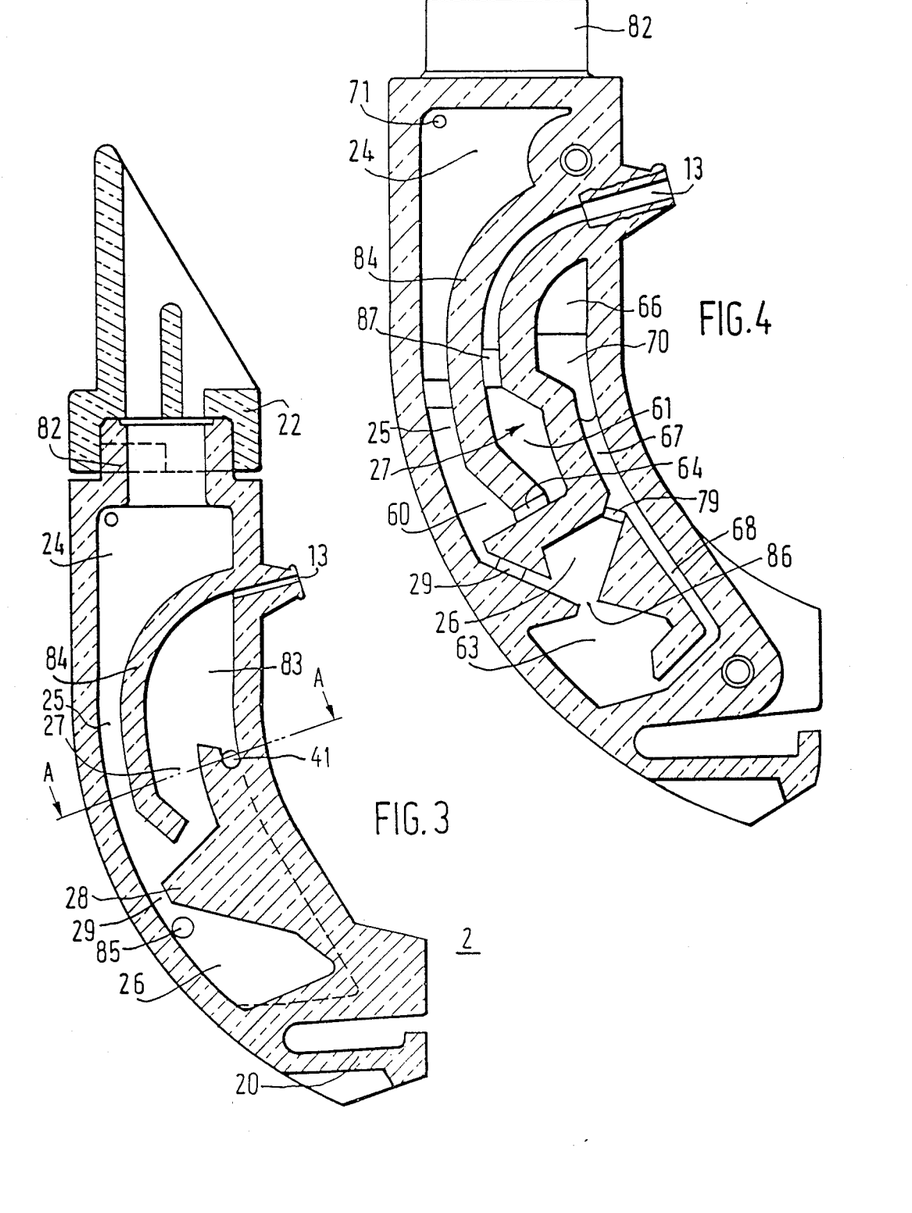
FIG. 3 is a section along the same plane of the cartridge belonging to a device according to FIG. 1.
FIG. 4 is a section of another embodiment of the cartridge according to the invention.

Before it is fixed to the casing (1), the said cartridge (2) is intended to collect the sample to be analyzed, whole blood in the present case. In order to do this, it possesses at its inlet (82) a removable sampling nozzle (22). Once the sample has been taken, the nozzle (22), which is simply inserted, is retracted and the separation cartridge (2) is clipped onto the casing (1), the inlet (82) which carried the sampling nozzle (22) first being inserted into a place provided for that purpose in the casing (1). A silicone stopper (23) is provided at this point, in order to seal the said cartridge (2) perfectly when the latter is in position on the casing (1). The cartridge is then clipped onto the casing by simple pressure.

Figure 3A:
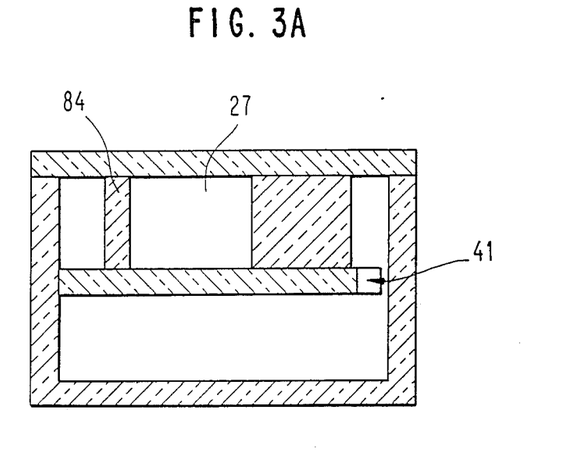
FIG. 3A is a cross-sectional view along line A—A of FIG. 3.

The separation cartridge (2), apart from the inlet (82), comprises at least two distinct chambers (27) and (26), which intercommunicate via a constricted or capillary passage (29), one (26) of the said chambers serving to collect, by means of centrifuging, the heavy fraction (red corpuscles) of the sample of whole blood, and the other (27) being intended to collect the light fraction (plasma). In the first chamber (27), a partition (84) defines on the one hand a capillary duct (25), communicating with the constricted passage (29), and a receptacle (24) for the sample of whole blood introduced through the inlet (82), and on the other hand a chamber (83) for draining the metered light fraction toward the capillary outlet (13) of the cartridge, and hence toward the calibration chamber (11) of the casing (1). The outlet (13) of the cartridge is positioned in the vicinity of its inlet (82), but separated from the latter by the partition (84). Moreover, the first chamber (27) communicates via a capillary aperture (41) with an overflow cell (FIG. 3A) positioned below the plane of circulation of the liquids, which plane is shown in FIG. 3.

In accordance with the foregoing description, and in the downward direction of the centrifugal force according to FIG. 3, and along the axis (3), the interaction of the chambers (26) and (27) with the duct (41) toward the overflow cell makes it possible both to meter the sample collected into the receptacle (24) and to separate the same sample into two fractions, one heavy and one light, by centrifuging.

The collecting chamber for the red corpuscles (26) is, in the upward direction of the centrifugal force and along the axis (3) according to FIG. 3, roughly sealed by means of a flap (85). The purpose of the latter is, when the centrifugal force is directed towards the stopper (23), to limit the flow of the red corpuscles toward the capillary (25), in a manner such that they can be sufficiently impelled toward the receptacle (24), and that it is quite impossible for them to pass into the chamber (27) containing the serum.

In contrast to the embodiment shown in FIG. 3, that shown in FIG. 4 makes it possible to improve the separation of the heavy and light fractions of the whole blood, and in particular not to remix them, when the metered light fraction is drained, under the action of the centrifugal force, toward the outlet (13) of the cartridge.

According to FIG. 4, and in contrast to FIG. 3:

the first chamber (27) for collecting the light fraction is divided into two sub-chambers, (60) and (61), separated at the level of the partition (84) by a capillary (64);

the sub-chamber (61) communicates with the outlet (13) via a capillary (87);

in addition to the first chamber (26) for collecting the heavy fraction, a second successive chamber (63) is provided which communicates with the first via a capillary (86);

each of the chambers (26) and (63) communicates, respectively by capillary apertures or ducts (79) and (68), with an overflow pre-cell (66), which in turn communicates, toward the lower part of the cartridge, with an overflow cell (not shown);

a vent (71) communicates directly with the overflow cell (not shown).

Consequently, as shown in FIG. 4, the cartridge (2) comprises two levels, an upper level, shown in this same figure, on which the liquids circulate under the action of the centrifugal force, and another, lower one which is at least partly allocated to the overflow cell.

In order to facilitate separation and avoid remixing, the sections of the various capillaries are adjusted relative to one another, in the following manner:

the capillary (86) has larger dimensions than those of the capillary (29);

the section of the capillary (25) is greater than that of the capillary (64), which favors the passage of the heavy constituents that may be present in the subchamber (60) toward the receptacle (24), rather than toward the subchamber (61), in the event that the centrifugal force is acting upward according to FIG. 4;

the section of the capillaries (67) and (79) is greater than that of the capillary (29), which favors the passage of the heavy constituents toward the overflow cell rather than toward the sub-chamber (60), in the event that the centrifugal force is acting in the same conditions as above.

FIGS. 11 to 16 illustrate the operation of the device according to the invention. A small incision having been made, for example at the tip of the finger or in the lobe of the ear, the separation cartridge (2) equipped with its sampling nozzle (22) is used to collect a few drops of blood. The said nozzle (22) is removed, and the said cartridge (2) is clipped onto the casing (1) as already described above (FIGS. 1 and 11).

Simultaneously, the push-button (18) (FIG. 8) of the reservoir assembly (7) is actuated, initiating firstly the irreversible clipping (91) of the said assembly into the operational or actuated position, and secondly the capillary aperture of the cover (40).

Figure 12:
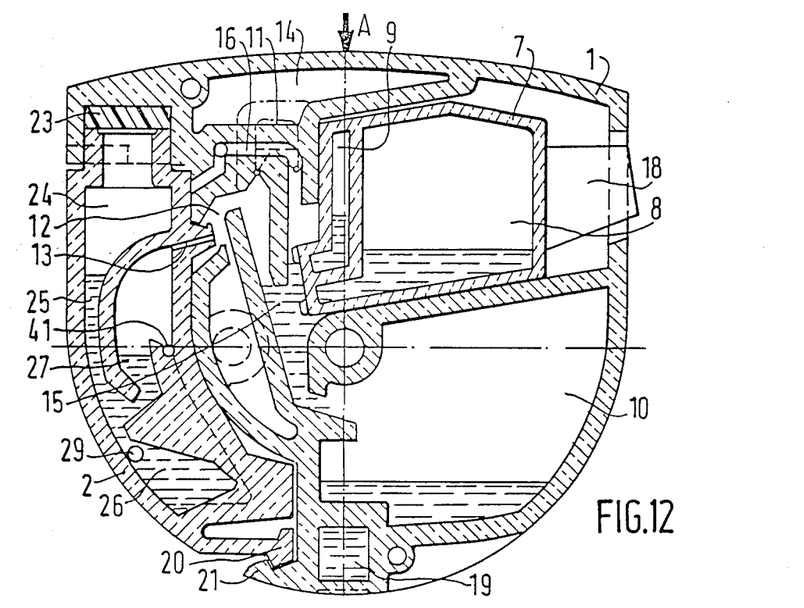
Figure 13:
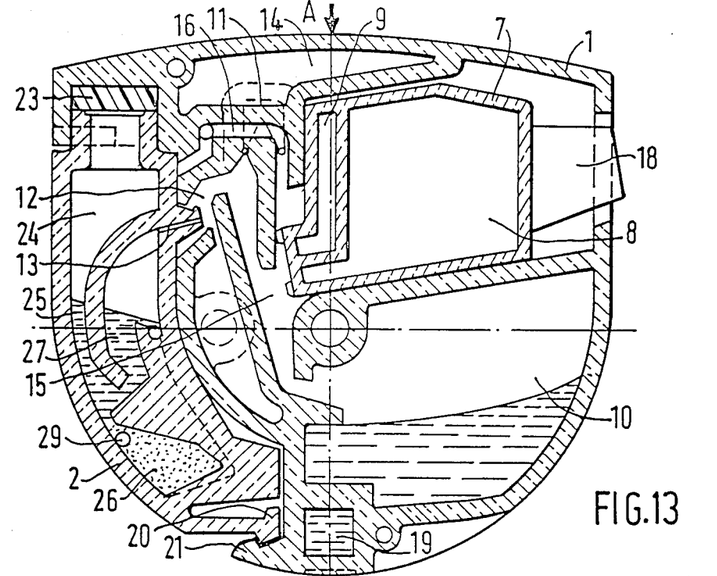

The device is then placed on the disk of a centrifuge, by means of two apertures (5, 6), and a first centrifuging operation is carried out, under the action of a centrifugal force directed in accordance with the arrow A, in other words following the median axis (3), downwards according to FIG. 12. This force A produces two effects.

Firstly, the diluent and the liquid reagent pass from their respective containers (8, 9) into the mixing chamber (10) via the transfer capillary (15);

Secondly, the blood passes, within the cartridge (2), from the receptacle (24) into the two chambers (26, 27), the excess blood or plasma being drained into the underlying overflow chamber via the aperture (41).

This first centrifuging operation (cf. FIG. 3) is continued for about 3 minutes, first in order to permit total homogenization (10) between the diluent (8) and the liquid reagent (9), and secondly and most importantly in order to permit the decantation of the blood into plasma and red corpuscles. The plasma, being of lower density than the red corpuscles, floats on the surface.

At this point, the serum has penetrated the first chamber (27). The red corpuscles are present in the second chamber (26). The centrifuge is then slowed, and a spectrophotometric measurement of the reagent is carried out at (19), this being referred to as the "blank reagent measurement". The optical density of the reagent is thus monitored, making it possible to verify that it is in a good state of preservation.

Figure 14:
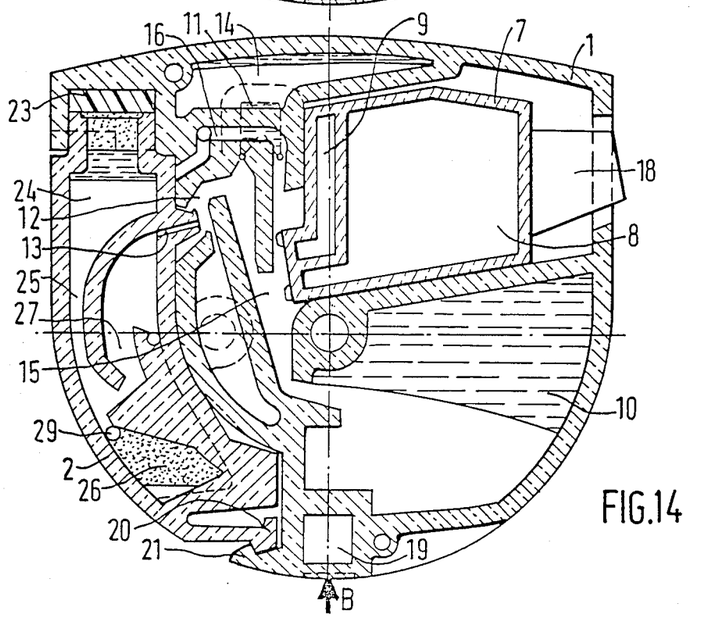

After stopping, the position of the device on the disk of the centrifuge is then inverted, and the direction of the centrifugal force is thus inverted, then being directed in accordance with the arrow B (FIG. 14). The reacted mixture is then still in the mixing chamber (10), and this repeated stirring further improves its homogenization with the diluent. The serum is impelled, via the outlet capillary (13), into the casing (1) and more precisely toward the calibration chamber (11). The excess serum is impelled by the centrifugal force via the capillary (16) into the serum overflow chamber (14). Moreover, the excess serum present in the capillary (25), together with the small quantities of red corpuscles which have escaped from the second chamber (26) are retained in the receptacle (24), which is sealed by the stopper (23).

Figure 15:
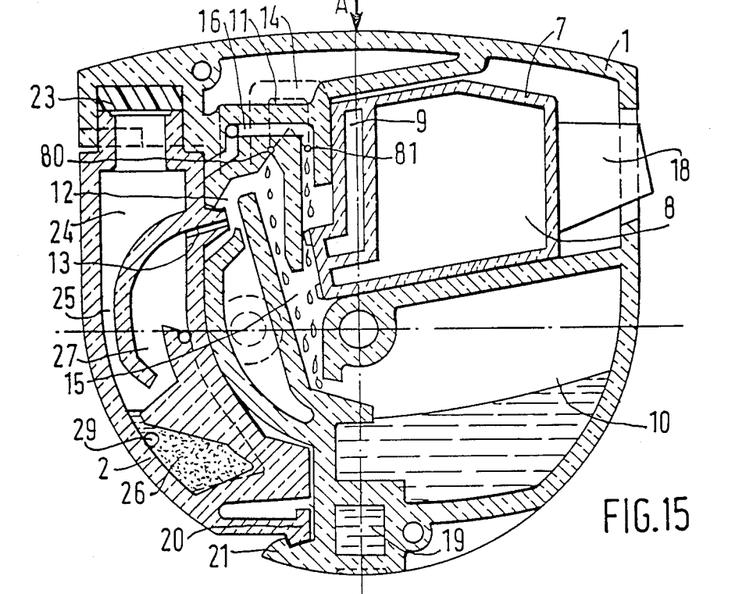
Figure 16:
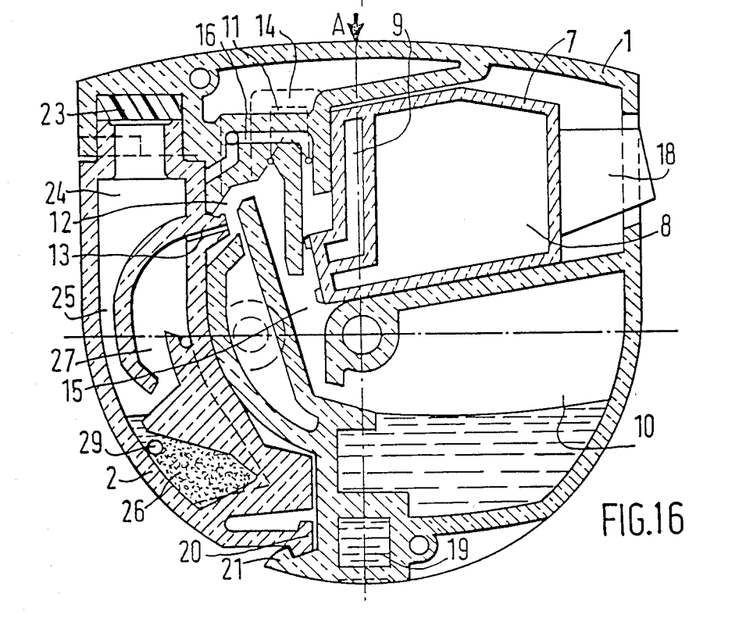

The device is re-inverted on the disk of the centrifuge, and the centrifugal force is re-inverted (arrow A) (FIG. 15). The serum is drained out of the calibration chamber (11) via the two parallel capillaries (34, 35), which rejoin the transfer capillary (15), and is routed into the mixing chamber (10). Homogenization with the reagent is ensured by an abrupt stopping operation, followed by immediate restarting of the centrifuge. The excess plasma and red corpuscles present in the receptacle (24) during the preceding stage are accumulated at the level of the chamber (27) and of the capillary (25) (FIG. 16).

Because the measurement cell (19) communicates freely with the mixing chamber (10), it contains the same product as the latter. In addition, the first spectrophotometric measurements are made in the first few seconds after mixing, in order to obtain a correct gradient value for the curve of optical density as a function of time. The optical density at saturation is then measured, to give the final curve. The gradient measurement is often necessary to enable correct conclusions to be drawn regarding the analyses carried out.

The above mode of operation results from the following arrangement of the device according to the invention in terms of circulation of the liquids according to the direction of centrifuging (principal axis (3)), in direction (A) or in the reverse direction (B):

in direction (A), the chambers (27), (26) and if appropriate (63) of the cartridge (2) are positioned downstream of one another;

in direction (B), the inlet (12) of the casing (1) is upstream of the capillary duct for introduction (80) toward the calibration chamber (11);

in direction (A), both the introduction (80) and drainage (81) ducts of the calibration chamber (11) and the container (7) for the reagent and/or the diluent are positioned upstream of the mixing chamber (10).

It should be noted that the invention is not limited to the use of liquid reagents. In fact, it is equally possible to use solid reagents, which are then placed in the mixing chamber (10) before the lid of the casing (1) is welded on. At the time of the first centrifuging operation, the diluent comes back into contact with the solid reagent in the said mixing chamber (10), which permits the reagent to dissolve during the decantation of the blood. No additional time is required for the dissolution, which it was impossible to achieve with the devices known hitherto.

I claim:

1. A device for analyzing a sample of a liquid comprising:
    a compartmented casing comprising an inlet, a container for at least one dose of a reagent of diluent, a chamber for calibration of a calibrated quantity obtained from the sample, and a chamber for mixing at least the calibrated quantity and the reagent of diluent, such that when said casing interacts with a centrifuging apparatus centrifugal force causes contents of the casing to circulate within the casing; and
    a cartridge including an inlet for directly introducing a sample into the cartridge from a source, a receptacle for collecting the introduced sample, means for metering the collected sample, said means for metering connected to the receptacle via a capillary duct extending into the casing, means for irreversibly clipping the cartridge to said casing, and an outlet passage communicating with the casing inlet when said cartridge is irreversibly clipped to said casing to pass a metered quantity from said cartridge to said casing, wherein said outlet of the cartridge is positioned in a vicinity of, but separate from, said cartridge inlet.

2. A device as claimed in claim 1, wherein the metering means incorporates means for separating the sample to be analyzed, by centrifuging, into at least two fractions, one light and one heavy, said means for separating permitting the light fraction of the sample to be drained toward the outlet of the cartridge, and an overflow cell connected to the metering means.

3. A device as claimed in claim 2, wherein the separating means comprises at least two distinct chambers interconnected via a constricted passage, and one of the two distinct chambers serves to collect the heavy fraction.

4. A device as claimed in claim 3, wherein the separating means comprises three chambers interconnected via at least two capillary passages, and two of the three chambers serve to collect, successively, the heavy fraction of the sample.

5. A device as claimed in claim 1, wherein the cartridge is bileveled and comprises a level on which the liquids circulate under the action of the centrifugal force, and a level which is at least partly allocated to the overflow cell.

6. A device as claimed in claim 1, wherein the calibration chamber is a metering siphon comprising two capillary ducts, one for introducing the metered quantity originating from the cartridge, and the other for draining the overflow, connected to an overflow chamber.

7. A device as claimed in claim 1, wherein the container for the reagent is contained within the casing, and can be displaced by pressure applied externally to said casing, from a first position in which the container is closed in a leaktight manner, to a second definitive activation position, in which a capillary aperture is opened in the container, toward the mixing chamber.

* * * * *

UNITED STATES PATENT AND TRADEMARK OFFICE
CERTIFICATE OF CORRECTION

PATENT NO. : 4,857,274
DATED : August 15, 1989
INVENTOR(S) : Jean-Pierre Simon

It is certified that error appears in the above-identified patent and that said Letters Patent is hereby corrected as shown below:

Claim 1, line 4, change "of" (second occurrence) to --or--;

line 8, change "of" to --or--.

Signed and Sealed this

Twelfth Day of March, 1991

*Attest:*

HARRY F. MANBECK, JR.

*Attesting Officer*      *Commissioner of Patents and Trademarks*